US012717174B2

(12) United States Patent
Caspari

(10) Patent No.: US 12,717,174 B2
(45) Date of Patent: Aug. 25, 2026

(54) PORTABLE LIGHT APPARATUS, CHARGING DEVICE FOR A PORTABLE LIGHT APPARATUS AND CONTROL SYSTEM FOR A PORTABLE LIGHT APPARATUS

(71) Applicant: HEALYAN GMBH, Barchfeld-Immelborn (DE)

(72) Inventor: Philipp Caspari, Barchfeld-Immelborn (DE)

(73) Assignee: HEALYAN GMBH, Barchfeld-Immelborn (DE)

( * ) Notice: Subject to any disclaimer, the term of this patent is extended or adjusted under 35 U.S.C. 154(b) by 0 days.

(21) Appl. No.: 19/213,936

(22) Filed: May 20, 2025

(65) Prior Publication Data

US 2025/0284146 A1 Sep. 11, 2025

Related U.S. Application Data

(62) Division of application No. 17/823,940, filed on Aug. 31, 2022, now Pat. No. 12,332,504.

(51) Int. Cl.
*G02C 11/04* (2006.01)
*A61N 5/06* (2006.01)
(Continued)

(52) U.S. Cl.
CPC ............ *G02C 11/04* (2013.01); *A61N 5/0618* (2013.01); *F21V 21/084* (2013.01); *F21V 33/0052* (2013.01); *G02C 5/001* (2013.01); *H02J 7/731* (2026.01); *H05B 47/165* (2020.01); *H05B 47/19* (2020.01); *A61N 2005/0626* (2013.01);
(Continued)

(58) Field of Classification Search
CPC .... A61N 5/0618; H05B 47/165; H05B 47/19; G02C 11/04
See application file for complete search history.

(56) References Cited

U.S. PATENT DOCUMENTS 6,235,046 B1 * 5/2001 Gerdt .................... A61M 21/00 600/26
10,935,815 B1 3/2021 Castañeda
(Continued)

FOREIGN PATENT DOCUMENTS

CA 3 013 871 A1 2/2020
CN 101912338 A 12/2010
(Continued)

OTHER PUBLICATIONS

European Search Report, dated of May 22, 2024, for corresponding European Patent Application No. 23194473.7 (11 pages).

*Primary Examiner* — Leah Macchiarolo
(74) *Attorney, Agent, or Firm* — INTELLECTUAL PROPERTY LAW GROUP LLP

(57) ABSTRACT

The invention relates to a portable light apparatus configured to be worn by a user, the portable light apparatus comprising a front frame to house eyeglasses and a pair of side frames connected to the front frame, an operating device having at least a battery and at least one auxiliary electronic part having a light device configured to emit light towards the eyeglasses and/or the user's eyes. Further, the invention relates to a charging case for a portable light apparatus and a control system providing remote control for a portable light apparatus.

20 Claims, 5 Drawing Sheets

(51) Int. Cl.

| | |
|---|---|
| ***F21V 21/084*** | (2006.01) |
| ***F21V 33/00*** | (2006.01) |
| ***G02C 5/00*** | (2006.01) |
| ***H02J 7/70*** | (2026.01) |
| ***H05B 47/165*** | (2020.01) |
| ***H05B 47/19*** | (2020.01) |
| *F21L 4/08* | (2006.01) |
| *G02C 7/10* | (2006.01) |

(52) U.S. Cl.
CPC ......... *A61N 2005/0648* (2013.01); *F21L 4/08* (2013.01); *G02C 7/10* (2013.01); *G02C 2200/08* (2013.01)

(56) References Cited

U.S. PATENT DOCUMENTS

| | | | | |
|---|---|---|---|---|
| 12,332,504 | B2* | 6/2025 | Caspari | F21V 33/0052 |
| 2004/0225340 | A1* | 11/2004 | Evans | A63B 23/185 607/88 |
| 2009/0005837 | A1 | 1/2009 | Olmstead | |
| 2010/0121158 | A1* | 5/2010 | Quevedo | A61N 5/0618 600/301 |
| 2012/0203310 | A1* | 8/2012 | Pugh | A61N 5/0618 607/93 |
| 2016/0016004 | A1 | 1/2016 | Hudson | |
| 2016/0144149 | A1 | 5/2016 | Pugh et al. | |
| 2017/0068120 | A1* | 3/2017 | Shiratori | H04M 1/05 |
| 2019/0179172 | A1 | 6/2019 | Schoutens et al. | |
| 2019/0331936 | A1* | 10/2019 | Allen | G03B 21/00 |
| 2020/0108270 | A1* | 4/2020 | LaVine | G02F 1/137 |
| 2020/0289321 | A1* | 9/2020 | Luo | A61B 5/4812 |
| 2021/0181534 | A1 | 6/2021 | Castañeda | |
| 2022/0008746 | A1 | 1/2022 | Malchano | |
| 2022/0155617 | A1 | 5/2022 | Smet et al. | |
| 2022/0179215 | A1 | 6/2022 | Jeon | |
| 2025/0065145 | A1* | 2/2025 | Tumlinson | A61N 5/0618 |

FOREIGN PATENT DOCUMENTS

| | | | |
|---|---|---|---|
| EP | 2 670 482 | B1 | 5/2015 |
| GB | 2 352 182 | A | 1/2001 |
| WO | WO 2020/070243 | A1 | 4/2020 |
| WO | WO 2020/164446 | A1 | 8/2020 |

* cited by examiner

PORTABLE LIGHT APPARATUS, CHARGING DEVICE FOR A PORTABLE LIGHT APPARATUS AND CONTROL SYSTEM FOR A PORTABLE LIGHT APPARATUS

CROSS-REFERENCE TO RELATED APPLICATION

This application is a divisional of commonly owned U.S. patent application Ser. No. 17/823,940 filed on Aug. 31, 2022, which is incorporated herein by reference in its entirety.

FIELD OF INVENTION

The invention relates to a portable light apparatus, for example glasses, to be worn by a user. The invention further relates to a charging device for a portable light apparatus, for example glasses to be worn by a user and a control system providing remote control for a portable light apparatus, for example glasses, to be worn by a user.

BACKGROUND

Sound and stroboscopic, such as light therapy, apparatuses are known which are being used for personal meditation and relaxation, for sleep improvement and visual and neural stimulus as well as medical applications. These range from treatments for psychological disorders like depression, anxiety, post-traumatic stress disorder to neurodegenerative diseases like Alzheimer's disease and Parkinson's disease.

Further, sound and light therapy has been established as an effective treatment for classic, or winter-based, seasonal affective disorders. Light therapy employs a device which emits significantly more candela than a standard incandescent lamp.

Known light therapy glasses have unflattering appearances that fit to the function of medical applications but lack of features to be worn as normal everyday glasses or sunglasses.

SUMMARY

It is an object of the present invention to provide an improved portable light apparatus, for example glasses, which improved light emitting features, light settings and which is improved in appearance such that the portable light apparatus may be worn as normal everyday glasses and/or sunglasses. The provided portable light apparatus of the present invention further allows flexibility in appearance and features, such as exchangeable glasses parts, for a user.

Another object of the present invention is to provide a charging case for a portable light apparatus, for example glasses, wherein the charging case is configured to hold and protect the portable light apparatus when not worn by a user and further provide charging features as well as a compact design.

Another object of the present invention is to provide a control system providing remote control for a portable light apparatus, such as glasses, so that the portable light apparatus may be controlled from remote devices to allow user engagement with the portable light apparatus and social engagement between individual customers for example on a centralized platform for their own portable light apparatus.

The object according to the portable light apparatus is achieved by the features of claim 1. The object according to the charging case is achieved by the features of claim 10 and the object according to the control system is achieved by the features of claim 16.

Preferred embodiments of the invention are given in the dependent claims.

A first embodiment relates to a portable light apparatus configured to be worn by a user, wherein the portable light apparatus comprises at least a front frame to house eye-glasses and a pair of side frames connected to the front frame, an operating device having at least a battery, at least one main electronic part and at least one auxiliary electronic part having a light device configured to emit light towards the eye-glasses and/or the user's eyes, wherein the battery is configured to supply energy to the light device via the electronic parts, wherein the main electronic part comprises a charging interface, in particular a charging port, to couple with an external charging device to recharge the battery and/or an external control device, for example for remote control of the portable light apparatus. The external control device may be a mobile device, a central server and/or a server-side, for example a so called back-end server, described later.

In some designs, the battery and the main electronic part are arranged in one of the side frames and the auxiliary electronic part with its light device is arranged in the front frame.

Emitted light radiation that is allowed to be directed towards the eye or eyeball is researched and defined by norms, for example regarding a maximum threshold of emitted light radiation and safety implications for the eyes regarding light sources, such as LED light sources, emitting visible optical radiation. Light sources and LEDs are consequently evaluated and categorized in terms of optical safety in accordance with the photobiological safety standards for different systems: IEC 62471 (International)/EN 62471 (EU) and ANSI/IESNA RP-27 (USA).

Care is taken to design the portable light apparatus such that it falls within these standards.

Further, these standards define a number of different Risk Groups (RGs) for light sources and LEDs. It is an object of the present invention to design the portable light apparatus such that it ensures safety to the user with no hazard, for example, no photobiological hazard, on exposure. These properties are defined, for example, by Risk Groups RG0 and RG1.

The light device is arranged in the front frame such that light emitted by the light device is directed towards the user's eye. There is no need for a reflection of the light off of the actual eyeglasses.

Light emitted by the light device may be guided along a shape of the front frame, in particular in an environment of the eyeglasses. Therefore, providing specific reflection elements to reflect the emitted light by the light device are not necessary. The emitted light is directly directed towards the user's eye.

According to a second embodiment, the portable light apparatus may comprise eyeglasses with reflecting properties, wherein the light device may be arranged such that light is emitted in a predefined angle towards the eyeglasses to reflect towards the user's eyes. The eyeglasses may be configured as light transmitting surfaces.

A third embodiment relates to a portable light apparatus configured to be worn by a user, wherein the portable light apparatus comprises at least a front frame to house eye-glasses and a pair of side frames connected to the front frame, an operating device having at least a battery and at least one auxiliary electronic part having a light device configured to emit light towards the eyeglasses and/or the user's eyes, wherein the battery is configured to supply energy to the light device via the auxiliary electronic part, wherein the battery is arranged in one of the side frames and the auxiliary electronic part and the light device are arranged in the front frame.

In some designs, the portable light apparatus is provided as light therapy apparatus, such as light therapy glasses to be worn by a user. The portable light apparatus may be provided as stroboscopic light therapy glasses. The portable light apparatus may be configured as regular glasses and/or sunglasses to be worn by a user.

The portable light apparatus has the advantage to have the appearance of a regular looking glasses, such as reading glasses, sunglasses and/or design glasses, whilst providing features of therapeutic and/or medical light applications, such as for personal meditation and relaxation, at any time the user is in need.

In some designs, the portable light apparatus is also suited for use to increase a concentration level and/or focus level, for example during work, sports, driving or any other activity.

The portable light apparatus, in particular light glasses, may also provide a fun factor to the user who may stand out with the apparatus when the light device is on, for example at events.

The user is not forced to exchange regular glasses with a portable light therapy device for therapeutic and/or medical light applications which reduces effort and time and make it simpler to use for the user. Therefore, the portable light apparatus according to the invention may also advantageously increase a frequency of use for the user. In some designs, for example, the portable light therapy device may comprise prescription lens and therefore additionally serve as both prescription glasses. In some designs, prescription lens in such a portable light therapy device may be photochromic, for example become darkened or colored under sunlight or high-intensity light. In some designs, the portable light apparatus has may comprise sunglasses, which may, for example, serve as a protective eyewear designed to prevent bright light from damaging or discomforting the eyes, for example by at least partially blocking UV radiation. The sunglasses may also reduce undesired distractions during the application of the disclosed portable light therapy device. In some designs, the light therapy device may comprise polarized glasses. In some designs, the glasses may additionally comprise blinders, for example to further minimize distractions during use. Such blinders may be attached either to the outer or to the inner side of the glasses.

The front frame and/or side frames, also known as temples, may have a shape, form, design and/or color and/or pattern desired by a fashion designer, a customer and/or a user.

The operating device may be configured to be adaptable to regular looking glasses frames and side frames. For example, in some configurations, the spectacle manufacturers, sellers and/or customers, may be able to easily retrofit existing spectacles and/or spectacle frames with the disclosed portable light operating device and/or adapt to the portable light operating device.

As disclosed, the eyeglasses for the portable light apparatus may be configured as regular transparent or colored glasses, ophthalmic grade glasses or lenses, color tinted glasses and/or functionally coated glasses. In some designs the eyeglasses may comprise anti glare, UV filters, polarisation filters, thermochromic or electrochromic coatings or any other coating and/or combination of all above. For clarity, the eyeglasses may have lenses with or without light attenuating function and/or visual acuity, in particular eyesight.

Advantages of electrochromic coated glasses may consist of providing different properties to the user such as lightly tinted glasses, fading properties, different colors which may be adjusted by means of a input device on the portable light apparatus and/or via a user interface on the mobile device connectable to the portable light apparatus. Furthermore, the electrochromic coated glasses may provide a so called shutter effect which may be adjustable. Electrochromic coatings may become dark when a voltage is applied and/or when charges are added to an optical part of the coating. When voltage and/or charges are removed, the coating may become transparent.

In some designs, it may be preferable for a total weight the portable light apparatus, with and/or without eyeglasses, to be in a certain range. Too heavy weight may induce discomfort and undesirably reduce the device usage. For example, in some designs, the total weight of the apparatus may preferably range from about 5 g to about 200 g, for example 10 g to 150 g. In some designs, the total weight of the portable light apparatus may range from about 20 g to 100 g to be in the most comfortable range for the user to apply it regularly.

In some designs, the auxiliary electronic part may be a printed circuit board (PCB). In some designs, the auxiliary electronic part may be a flexible printed circuit board (flexible PCB, FPCB) which has an outline shape of the front frame. The auxiliary electronic part may be configured as a flexible cable or a flexible plate.

In some designs, the auxiliary electronic part may be a purely flexible PCB or a rigid PCB. The auxiliary electronic part may consist of at least one rigid PCB and at least one flexible PCB. The auxiliary electronic part may consist of two rigid PCBs connected by at least one flexible PCB. The auxiliary electronic part may consist of at least two flexible PCBs connected by at least one flexible or rigid PCB. The PCBs of the auxiliary electronic part may be connected to each other by a number of cables, such as individual cables or in form of a ribbon cable. Therefore, a stable connection between the PCBs of the auxiliary electronic part may be easily achieved.

In some designs, a connection between the main electronic part and the auxiliary electronic part may be connected to each other by a number of cables, for example a number of individual cables or in form of a ribbon cable. Therefore, a stable connection between the main electronic part and the auxiliary electronic part in a connection area of the front frame to the side frame may be easily achieved.

In some designs, the auxiliary electronic part may be configured reversibly flexible and/or elastic. The auxiliary electronic part may be a reversibly flexible and/or elastic PCB. Thereby, the auxiliary electronic part may be formed adaptable or designed to fit the front frame, for example to movements and/or bends of the front frame and/or the side frame. Conductive paths may be configured meander-shaped or the like, providing flexible and/or elastic and/or bending properties.

In some designs, the auxiliary electronic part may be configured stretchable. The auxiliary electronic part may be a stretchable PCB. The auxiliary electronic part may be made of thermoplastic polyurethane. Conductive paths may be configured meander-shaped or the like, providing flexible and/or elastic and/or bending properties.

The auxiliary electronic part may comprise a shape with cutouts of the shape of the eyeglasses to not block the user's vision through the eyeglasses held by the front frame. In some designs, the auxiliary electronic part may be substantially plate-shaped and comprises at least one cutout in the shape of the front frame.

In some designs, the auxiliary electronic part may be substantially circular-shaped or semicircular-shaped or square-shaped or may comprise any other shape. The auxiliary electronic part may be configured to follow an outline of the front frame. The auxiliary electronic part may comprise two cutouts, one for a left eyeglass and one for the right eyeglass. In another embodiment, two auxiliary electronic parts may be used, each one for each eyeglass area in the front frame.

In some designs, the auxiliary electronic part may comprise at least one bent area in a nose bridge area, a bent area in a connection area to at least one of the side frames and/or in an area of at least one light emitting diode of the light device.

In some designs, connector elements, such as connector pins, contact pins or electrical connectors or electrical pins and corresponding connector sockets or contact holes, may be used in the connection area between the front frame and at least one of the side frame providing a releasable connection of the main electronic part and the auxiliary electronic part. The connector elements may be spring-loaded.

One end of the main electronic part, which is arranged in the at least one side frame, may comprise a number of first connector elements, facing towards the front frame. One end of the auxiliary electronic part, which is arranged in the front frame, may comprise a number of second connector elements corresponding to the first connector elements, facing towards the at least one side frame. In a use state of the portable light apparatus to be worn by the user, the connector elements are engaged, wherein the main electronic part and the auxiliary electronic part are in electrical connection. In a non-use state or stowed state of the portable light apparatus, the connector elements are disengaged.

Alternatively or optionally additionally, the electrical connection interface, releasable or non-releasable, for example temporary or permanent connections, is provided by a number of cables and/or other connector elements, such as plug blades.

A suitable bend radius of the auxiliary electronic part may be in a range of a few millimeters. A bend radius may be selected depending on a total thickness of the printed circuit board. In some designs, the bend radius may range from about 0.1 mm or greater to any needed and/or desired value, and direct emitted light by the light device towards the user's eye. In some designs, the auxiliary electronic part, in particular in form of a flexible printed circuit board, between the front frame and the corresponding side frame may be bent about a predefined radius of a few millimeters.

The bend radius at the connection area, in particular connection interface part, of the frame part to at least one of the side frames may be in a range of a few millimeters. In some designs, the bend radius may range from 0.1 mm or greater to any needed and/or desired value.

The flexible auxiliary electronic part may comprise at least one stiffener layer located at least in an area underneath the light device, in particular underneath each light emitting diode (LED) of the light device. The light device comprises at least one light emitting diode (LED) soldered or otherwise attached thereto.

The maximum light intensity (total radiance of the light device—radiance being the radiant flux per unit solid angle per unit projected area) of all of the LEDs in the portable light apparatus combined may preferably range from about 0.0001 W/(m$^2$*sr) to about 4*10$^6$ W/(m$^2$*sr) for electromagnetic radiation in the wavelength range of 150 nm to 3000 nm. Too low intensity may reduce the impact of the device, while to high intensity may induce discomfort or various undesirable side effects. The maximum light intensity of the individual LED may also preferably range from about 0.0005 W/(m$^2$*sr) to about 0,001 W/(m$^2$*sr). Too high intensity of the individual LED may similarly lead to discomfort or side effects.

The total number of the LEDs may range from 1 to about 1000,000. The larger number of LEDs may enable a smoother effect for the user because a more evenly distributed illumination of the area of the user's eye can be achieved, but often at the expense of additional cost or complexity. The suitable size of the LEDs footprint may range from about 1 μm$^2$ to about 100 mm$^2$.

In some designs, the spacing between the individual LEDs may range from about 0.01 μm to about 100 mm.

Examples of suitable LEDs include but are not limited to the standard package sizes referred to as: 0204, 0603, 0805. These standardized sizes allow for a reduction in production cost of the portable light apparatus, while being large enough to output enough light to create the desired effect.

In some designs the LEDs can be arranged in an array that utilizes organic light emitting diodes (OLEDs), forming one surface that can appear to the user's eye coherent, so that the user is unable to identify a single LED or OLED with the naked eye. One example of such an array may commonly be referred to as an OLED display. The application of an OLED display into the portable light apparatus would benefit the freedom of design.

In some designs LEDs with a di-, tri, tetra- or multichromatic spectrum may increase the luminous efficacy of the portable light apparatus. In other designs LEDs with a variable wavelength output spectrum might be utilized. Packages that include RGB LEDs may be utilized to enhance certain stimuli for the user according to their wishes. As an example, the increased output of blue light can lead to an increased output of the hormone and neurotransmitter Serotonin, which in return may help the user waking up in the morning.

The light emitting diodes may utilize but are not limited to the following base materials and Elements to radiate electromagnetic waves in the wavelength range of 150 nm to 3000 nm: GaN—Galium Nitride, InGaN—Indium Galium Nitride, Saphire, ZnSe—Zinc Selenide, Si—Silicone, InGaN—Indium Galium Nitride, P—Phosphorous, YAG—doped Yttrium Aluminium Garnet, AlGaN—Aluminium Galium Nitride, AlGaInN—Aluminium Galium Indium Nitride, BN—Boron Nitride, organic compounds like organic molecules in a crystalline phase including polymers.

In some designs the light output of the LEDs may be altered by the package the LED is manufactured with. One example of this may be a polymer lens that alters the output spectrum and directs the light into a desired direction. Also, reflective layers within the LEDs package may be utilized to direct the light towards the user.

In some designs, the LED may be arranged in a cutout, recess, opening or the like provided in the auxiliary electronic part. The LED, for example, may comprise one end which is soldered or otherwise attached to the auxiliary electronic part, for example to a region which has a bend, and another end which is arranged in the cutout.

In some designs, a stiffener layer may be located on the auxiliary electronic part at least in an area underneath, above or both at the bent area of the connection area to at least one of the side frames.

In some designs low powered LASERs with the output range of 0.0001 W/($m^2$*sr) to about 4*$10^6$ W/($m^2$*sr) may be utilized. The emitted monochromatic coherent radiation can be directed towards the user's eye utilizing no lenses, a collimating lens, or multiple lenses to form the beam in a useful manner to create the desired effect of the portable light apparatus.

In some designs, a stiffener layer may be located on the auxiliary electronic part at least in a connection area of the auxiliary electronic part to a main electronic part, such as a main printed circuit board (PCB) which will be specified later, wherein the main electronic part is arranged in at least one of the side frames. This area corresponds to the connection area of the front frame to at least one of the side frames.

In some designs, the front frame may comprise two frame parts permanently or temporarily connected to one another to hold the eyeglasses. In one configuration, the front frame parts are connected to each other in a material-locking manner, force-locking manner and/or form-locking manner.

In some designs, the magnet may exhibit one or more of the following compositions: NdFeB—Neodymium Iron Boron, AlNiCo—Aluminium Nickel Chromium, SmCo—Samarium Cobalt, BiMo—Bismuth Mangan, Ferrite and other Iron based alloys. The "strength"—also referred to as maximum energy product, meaning the energy density of the individual magnet may range from about 10 KJ/$m^3$ to about 3000 KJ/$m^3$. The size of the individual magnets may range from a volume of about 1 $mm^3$ to about 1000 $mm^3$. The excessive magnet size may undesirably increase weight or aesthetics. The excessive magnet strength may similarly be uncomfortable, and create electromagnetic interference, while too low strength may reduce the functionality of the joining technique.

In some designs, the frame parts may be joined together with screws, magnets, snap fittings, glue, friction welding, overmolding or any other temporarily or permanent joining technique.

In some designs, if the front frame parts may be temporarily connected to each other via a force-locking manner, also known as force-fitting manner, the eyeglasses may be exchanged by separating the frame parts. In some designs, such temporary connections may enhance the operational flexibility and provide superior user experience.

In some designs, the separate pieces, namely the frame parts, may be configured to hold the eyeglasses and the auxiliary electronic part with its light device. The frame parts may be manufactured, for example, by using injection molding, additive manufacturing, vacuum forming, milling or any other manufacturing method.

In some designs, in a detached state of the front frame, in particular the frame parts, the eyeglasses may be exchangeable and wherein the auxiliary electronic part and the light device are fixedly arranged in one of the frame parts. The auxiliary electronic part with its light device is held in place by one of the frame parts.

In some designs, the front frame is mechanically connected to the side frames, for example via a hinge joint or any other hinge and/or joint mechanism. The side frames are foldable in a direction towards and away from the front frame. In some designs, one of the frame parts is connected to the side frames via a respective hinge joint.

In some designs, the at least one side frame comprising the main electronic part may be connected to the front frame via a connection mechanism with more than one degree of freedom. The connection mechanism may be configured as a hinge and slide mechanism, for example a rotary-sliding hinge. In some designs, a pivot joint is configured as a sliding joint at the same time, wherein pivot movement of the side frame relative to the front frame, when folding from the use state to the non-use state of glasses, causes the side frame to slide relative to the front frame. Not only a user experience may be improved, but maintaining a permanent electrical connection between the main electronic part and the auxiliary electronic part or connecting and disconnecting a releasable electrical connection between the electronic parts may be simplified. Furthermore, the connection mechanism with more than one degree of freedom may compensate different head sizes as well as reducing a distance between the side frame and the front frame so as to reduce folding and/or bending of an electrical connection interface between the main electronic part and the auxiliary electronic part.

In some designs, at least one of the side frames may hold one or more batteries and the main electronic part of the operating device. In some designs, at least one of the side frames may comprise a mechanical power switch to connect a circuit of the main electronic part to the at least one battery. In some designs, at least one of the side frames may comprise a charging port to recharge the one or more batteries, for example such as lithium-ion batteries, from an external charging device, in particular an external power source.

In some designs, the at least one side frame may hold lithium-ion or lithium metal batteries, such as pouch-type, coin-type, cylindrical-type or prismatic-type batteries, and the main electronic part. The use of lithium-ion or lithium metal batteries may enable high specific energy, long cycle life, long calendar life and other advantages often lacking in other battery chemistries. In some designs, the cathode in such batteries may preferably comprise layered lithium cobalt oxide (LCO) or lithium nickel cobalt manganese oxide (NCM) to enable sufficiently high energy density.

In some designs, the operating device may comprise at least one main electronic part, namely the main printed circuit board, which may be arranged in one of the side frames having a number of interfaces, wherein a first interface providing a connection to the auxiliary electronic part, a second interface providing a connection to the battery and at least a third interface providing connection to an external charging device.

In some designs, the main electronic part may hold the first interface, in particular a communication interface, that permanently or temporarily connects the main electronic part located in one of the side frames to the flexible auxiliary electronic part located in the front frame. The main electronic part may hold the second interface, for example a power line, that permanently or temporarily connects the main electronic part to the battery. The main electronic part may hold the third interface, for example a communication interface, that is able to connect to the external charging device when, for example, the portable light apparatus is coupled to a charging device. The portable light apparatus may be charged wirelessly or wired. The wireless charging may be preferable in some designs, as it may enhance user experience, because classic wired solutions like cables and contact pins are prone to wear and degradation over time the wireless charging capability might increase the lifespan of the portable light apparatus.

In some designs, the operating device may comprise at least a processor module, a light device driver and a voltage regulation circuit and battery charging circuit, a charging connector and/or a power switch. The main electronic part may comprise the processor module, the light device driver and the voltage regulation circuit and battery charging circuit, the charging connector and/or the power switch as electronic components.

The main electronic part may hold a communication chip with at least one or more processing cores, for example configured as the processor module, and a radio module, such as a communication interface, to transmit and exchange data using radio waves. In some designs, the radio module may be configured to transmit and exchange data using low energy. This is, for example, known from audio streaming over radio waves. The radio module is configured to communicate via audio data. The radio module is configured to communicate over a low energy connection with reduced power consumption.

In some designs, the radio module may be configured to communicate over a so called Bluetooth Low Energy (BLE) connection. BLE is a wireless network technology standard intended to provide considerably reduced power consumption while maintaining a defined communication range. BLE is configured to exchange data over a defined distance between Bluetooth-compatible devices, including fixed and mobile devices.

In some designs, the operating device may comprise a light device driver to control stroboscopic frequency and/or light sequences of the light device in the front frame. The main electronic part may hold a multi-channel driver chip, for example configured as the light device driver, to receive logic level signals, for example between 0.1 and 100 Hz, from the communication chip to control stroboscopic frequency, for example for generating a light sequence, of the light device in the front frame. Further, the stroboscopic frequency may be adjusted. In some designs, adjustment steps may be about 0.01 Hz for a "smooth experience".

In some designs, the main electronic part may hold a power transistor, such as a single power transistor, to receive a signal, such as a pulse-width-modulation signal, from the communication chip to control a power level, in particular energy level, of the light device in the front frame.

In some designs, the main electronic part may hold the voltage regulation circuit to power, that means to supply energy to the communication chip and the light device on the auxiliary electronic part.

Further, the main electronic part may hold the battery charging circuit and a charging controller circuit to recharge the at least one battery located in at least one of the side frames.

In some designs, the operating device comprises a communication interface providing connection to a mobile device, a central server and/or a back-end device to exchange user data. The main electronic part may hold the communication interface. The communication interface may be provided to remotely control the operating device from the mobile device and/or the central server and/or the server-side device.

The operating device may communicate with the mobile device and/or the central server to analyze, for example, played audio files on the mobile device and/or the central server and, based on user settings, to synchronize and/or generate an appropriate light frequency and/or light sequence of the light device according to the audio listened by the user. A combination of audio listened by the user and light effects applied to the user has been surprisingly effective for therapy.

In summary: It is object of the invention to miniaturize and integrate electronics to an operating device so it may be put into regular looking glasses frames and temples. The stroboscopic light effects will be generated by direct or indirect light sources, for example coming from suitable light emitting diodes (LEDs) that sit inside the front frame part so vision of the user is not blocked and the glasses may be worn as normal everyday glasses or sunglasses. The glasses may be equipped with tinted glasses or ophthalmic grade lenses. To change and integrate the glasses and/or lenses of choice inside the front frame, it may be split up into two frame parts so the glasses/lenses may be placed in one frame half and the other half is placed on top, to form a cavity around the glasses/lenses circumference to hold the glasses/lenses in place. To achieve a fashionable, modern and neutral look the LEDs may be supplied with electrical energy using minimal space inside the front frame for supply lines. Because of its needed size, the battery to supply the LEDs with electrical power has to be located in the temple. To electrically connect the components inside the temple and the flexible PCB in the front frame, spring loaded pins may be used and opposing target connector surfaces. In another example to electrically connect the components inside the temple and the flexible PCB in the front frame a flexible ribbon connector cable may be used between the two PCBs, namely the main printed circuit board and the auxiliary printed circuit board. In another example to electrically connect the components inside the temple and the flexible PCB in the front frame a permanent flexible connection piece may be integrated into the flexible LED-PCBs side. The circuitry integrated into the portable light apparatus comprises a charging system for the battery, such as a common Li-battery, the main processing chip module with integrated antenna, the LEDs and LED-driver chips as power regulators, and a voltage regulation system supplying the main processor, LED drivers and LEDs. The portable light apparatus has a power switch, so all the electrical components except the charging circuitry may be permanently disconnected from the battery supplying them. On the same temple, a pair of charging target connectors may be located so the portable light apparatus may be charged with spring loaded connectors when they are placed inside a dedicated charging device, such as a charging case as introduced later. Alternatively or optionally additionally, the portable light apparatus may be charged via a charging cable with or without the case. Furthermore, the portable light apparatus may be equipped with a magnetic charging device, for example such as a magnetic snap or clamp device to interact with a magnetic charging cable.

The charging case according to the invention for a portable light apparatus which is configured to be worn by a user, may comprise at least a housing having a cavity in which the portable light apparatus is insertable to be held and protected, and a charging operating device arranged in the housing, wherein the charging operating device is configured to charge a battery of the portable light apparatus when inserted in the cavity.

In some designs, the charging case may comprise at least one battery, for example a rechargeable battery, to charge the at least one battery of the portable light apparatus.

The charging case has the advantage to be portable and to provide storage and protection for the portable light apparatus, in particular in form of glasses. The user may use the charging case as a regular storage and protection case. The charging case enables the user to recharge the portable light apparatus in a simple and comfortable manner. The charging case may have the appearance of a regular glasses case.

The charging case may comprise at least one compartment for storing a number of different exchangeable eyeglasses for the portable light apparatus. In some designs, the housing may comprise a separate compartment below or above the cavity in which the portable light apparatus is insertable. Therefore, the user carrying the charging case may adapt the portable light apparatus to different needs and purposes. The portable light apparatus may be used as regular glasses or sunglasses.

In some designs, the portable light apparatus configured to be worn by a user may comprise a front frame to house eyeglasses and a pair of side frames connected to the front frame, an operating device having at least a battery, at least one auxiliary electronic part having a light device configured to emit light towards the eyeglasses and/or the user's eyes, wherein the battery may be configured to supply energy to the light device via the auxiliary electronic part, wherein the operating device is partially or completely arranged in one of the side frames and/or in the front frame. In some designs, the battery may be arranged in one of the side frames and the auxiliary electronic part and the light device may be arranged in the front frame and/or one of the side frames.

The portable light apparatus may comprise any feature of described embodiments and combination of features as described above.

In some designs, the housing, in particular a shell, of the charging case may comprise two corresponding housing parts, wherein one of the housing parts forms the cavity and the other one of the housing parts is configured as a lid to close or open the cavity. The housing parts may be connected to each other by a hinge joint to form the cavity that may be opened and closed.

In some designs, the housing may comprise a separation line between the two housing parts. A notch may be located at the separation line.

In some designs, the housing parts may contain magnets that are oriented to attract the respective parts. The cavity may be formed by the hinge-connected housing parts. The cavity cannot open on its own while the charging case is oriented in any direction.

In some designs, the cavity may be formed such that an insert direction of the portable light apparatus is defined for the user. The cavity may be shaped such that the portable light apparatus is tightly inserted and fitted when arranged in the cavity. The specified insert direction may refer to a specified folding configuration of the side frames.

In some designs, at least one of the housing parts may comprise a holding element configured to guide the user to insert and place the light apparatus and to removably hold the portable light apparatus in place in the cavity. The cavity, in particular an opening of the cavity, may be oriented in one direction. The cavity may be upholstered.

In some designs, the holding element may be a magnet element. The holding element may be configured to guide the user to place the portable light apparatus into the cavity and to hold the portable light apparatus in place.

The housing parts may be manufactured using injection molding, additive manufacturing, vacuum forming, milling or any other suitable manufacturing method.

Additional pieces to the housing parts may be permanently or temporarily joined with screws, magnets, snap fittings, glue, friction welding, overmolding or any other temporary or permanent joining techniques.

In some designs, the housing comprises at least one charging port to establish a temporary electrical connection to the portable light apparatus.

In some designs, at least one of the housing parts may hold charging electronics for charging the battery of the portable light apparatus. At least one of the housing parts may hold a corresponding counterpart to a charging interface, in particular a charging port, of the portable light apparatus to establish a temporary electrical connection.

Further, the housing, for example one of the housing parts, may comprise at least one display device to display a battery status of the charging case and/or the portable light apparatus. The display device may be configured to give the user a visual feedback about a charging status of the portable light apparatus and/or of a battery of the charging case itself. The charging case may, for example, be rechargeable. The charging case may comprise a charging interface to connect to an external charging device. The charging case may comprise a battery, for example a lithium-ion battery. In some designs, one of the housing parts may comprise at least one cutout for the display device and/or another electrical element that displays the battery status.

In some designs, the charging electronics of the charging case may comprise at least one printed circuit board (PCB). The charging electronics may comprise at least one rechargeable battery. The charging electronics may comprise a charging circuit accessible wired, for example via a so called Universal Serial Bus (USB), to recharge the at least one battery of the charging case. The charging electronics may comprise at least one voltage level regulating circuit to provide correct voltage and power to recharge the battery of the charging case. The charging electronics may comprise a charging port that connects to a corresponding port of the portable light apparatus. Further, the charging electronics may comprise the display device, for example an indicator element, to visually display the battery level of the at least one battery inside the charging case.

In summary: The charging case may contain a battery and PCB circuitry, to be charged using a USB-Type-Standard. The voltage of the battery inside the charging case may be stepped up to a standard, for example, a standard 5V USB voltage level and supplied to the spring loaded pins located inside the case, so it may charge the portable light apparatus when they are connected by placing them inside the charging case. The positioning of the portable light apparatus in the charging case may be taken care of, by placing, for example, permanent magnets inside the frames, such as the front frame and/or the temples of the portable light apparatus, and the charging case that are configured to attract each other.

The control system according to the invention providing remote control for a portable light apparatus to be worn by a user, may comprise at least a light sequencing algorithm and a communication interface providing connection to a mobile device and/or a central server, wherein depending on data transmitted from the mobile device and/or the central server to the communication interface the light sequencing algorithm generates a light sequence for the portable light apparatus.

The control system has the advantage to be compact in design and so as to be easily integrated into a glasses frame design as well as providing reliable wireless or wired connection to the mobile device and/or a central server to exchange data.

The control system may further allow remote control for the portable light apparatus, such as glasses, so that the portable light apparatus may be controlled from remote devices to allow a simple user interface. Furthermore, the control system may be configured to enable user engagement with the portable light apparatus and social engagement between individual customers for example on a centralized platform for their own portable light apparatus which will be described later.

The control system may be configured as a processor module integrated in the portable light apparatus, for example to an operating device, in particular to a main printed circuit board (PCB) which runs the portable light apparatus. The control system may be software provided on the operating device, in particular on the main PCB, of the portable light apparatus.

The portable light apparatus configured to be worn by a user may comprise a front frame to house eyeglasses and a pair of side frames connected to the front frame, an operating device having at least a battery, at least one auxiliary electronic part having a light device configured to emit light towards the eyeglasses and/or the user's eyes, wherein the battery is configured to supply energy to the light device via the auxiliary electronic part, wherein the operating device is partially or completely arranged in one of the side frames and/or in the front frame. For example, the battery may be arranged in one of the side frames and the auxiliary electronic part and the light device are arranged in the front frame and/or one of the side frames. The portable light apparatus may comprise any feature of embodiments and combination of features as described above.

In some designs, the operating device may comprise at least one main electronic part, namely the main printed circuit board, which may be arranged in one of the side frames having a number of interfaces, wherein a first interface providing a connection to the auxiliary electronic part and a second interface providing a connection to the battery.

The main electronic part may hold a communication chip with at least one or more processing cores, for example configured as the processor module, and a radio module, such as a communication interface, to transmit and exchange data using radio waves. In some designs, the radio module may be configured to transmit and exchange data using low energy. This is, for example, known from audio streaming over radio waves.

In some designs, the control system may be running on the communication chip of the portable light apparatus or on a separate chip not yet integrated to an apparatus.

In some designs, the control system may be configured to be responsible to process at least one of the following described tasks. The control system may be configured to receive audio data from an external source, such as the mobile device and/or the central server, via radio waves. The control system may be configured to transmit the received audio data to an audio amplifier or audio output device, for example a loudspeaker or bone sound transducer. The control system may be configured to share or forward data with devices that use the same radio wave communication technology. Examples for other devices may be: transcutaneous electrical nerve stimulation device and/or an electric actuator creating oscillations that may be felt by the user via touch. Furthermore, for example, piezo actuators and/or an electric motor can be used to create oscillations that may be felt by the user via touch and/or have other effects other than being felt via touch.

The control system may be configured to manage over software updates, wireless or wired. The control system may be configured to retrieve, collect and exchange user data with the external source based on user settings. The control system may be configured to store user input variables necessary to generate light sequences of the light device of the portable light apparatus. The control system may comprise a user authorization and activation based on input data from the mobile device and/or the central server, for example from an application and/or client-side, and/or from a server-side, for example a server-side database or a so called back-end server where data and source codes may be programmed, updated, managed and stored.

The control system may be configured to receive measurements of bio sensors. The control system may comprise a bio sensor feedback integration that takes live sensor measurement data into account to fine-tune the light sequences of the portable light apparatus to further enhance the user experience. Those Sensors may be, but are not limited to: heartrate sensor, blood pressure sensor, blood oxygen sensor, EEG—electroencephalography measurement data and fMRI—functional magnetic resonance imaging data.

In some designs, the control system may communicate with the mobile device and/or the central server to analyze, for example, played audio files on the mobile device and/or the central server and, based on user settings, to advantageously, for example for a more favourable user experience and enhanced affect, synchronize and/or generate an appropriate light frequency and/or light sequence of the light device according to the audio listened by the user. A combination of audio listened by the user and light effects applied to the user has been surprisingly effective for therapy.

The mobile device may be a smartphone or a tablet or a smartwatch or the like. The central server may be provided by an application (so called APP) on a computer and/or mobile device. The central server or client-side may run on a user's device through which user interface the user may interact with the portable light apparatus and/or server-side.

The application, such as a smartphone application, also known as APP (short), may be adapted to run on different operating systems of mobile devices.

Graphical details of a user interface may vary on each of those operating systems. The user interface may consist of at least four sections, such as "Home", "Search", "Sequence" and "Account".

In some designs, in the section "Home" the user may have the ability to engage in at least the following interactions: see a timeframe based overview of personal use of different frequency bands at least daily, weekly, monthly and annually; manage own sequenced audio tracks, playlists and albums as well as those of other users they follow which are made public by those users; interact, such as known "like" and "comment" interactions, with news feed filled with at least latest tracks, playlists, albums and posts based on users they follow.

In some designs, in the section "Search" the user may have the ability to engage in at least the following interactions: search specifically at least for publicly available tracks, playlists, albums and other publicly shared user profiles; see suggested music titles and/or audio titles, for example audio book titles and audio track titles, based on genres from at least one and not limited to known platforms and/or providers; see a set of suggested sequencing settings, in particular light frequency and/or sequence settings, for each of the music and/or audio files.

In some designs, in the section "Sequence" the user may have the ability to engage in at least the following interactions: create their own set of individual sequencing settings for personal use and/or shared use; transmit those settings to their own portable light apparatus, store the settings in the application and/or in the server side database; link their chosen sequencing settings to music and/or audio tracks, playlists and/or albums; create a set of different settings that are linked to music and/or audio tracks, playlists and/or albums; create a set of different settings that a linked to music and/or audio tracks, playlists and/or albums with dedicated comments and recommendations of use.

In some designs, in the section "Account" the user may have the ability to engage in at least the following interactions: activate their portable light apparatus; manage their subscription; manage profile settings at least for privacy and social interaction.

The application may advantageously have an application programming interface (API) which is configured to exchange data with the server side database at least but not limited to the following: user account and payment info; user sequencing settings data; duration of use; type of use.

The API may be configured to exchange data also with APIs from third party streaming providers from at least one and not limited to platforms and/or providers.

The server-side database may consist of at least the following elements and is not limited to them: an application programming interface (API) for the application, in particular the mobile device application; data management unit; secure private customer payment info data storage; sequencing settings data storage for public tracks, playlists and albums; high bandwidth interface to manage quick service accessibility.

The server-side database may have an own dedicated hardware with multiple backups of all the stored data with continuously performed data backups.

The communication interface may comprise at least a transmitting unit and a receiving unit to retrieve, collect and exchange data with the mobile device and/or the central server.

In some designs, the communication interface may be configured to provide communication to a back-end device, for example providing a server side database.

In some designs, the light sequencing algorithm may be configured to generate light sequences based on received audio data and/or synchronous to music files and/or audio files playing on the mobile device and/or the central server and/or sensor measurement data and/or user input data.

In some designs, the light sequencing algorithm may be configured to generate light sequences based on received audio data and/or user settings.

In some designs, the light sequencing algorithm may be configured to analyze audio data packages that are received via radio waves, for example on low energy and/or via BLE connection, on the fly, meaning as soon as they arrive. Information generated based on the analyzed audio data packages alongside the input of a number of user input variables from the sequencing settings may then be used to generate light sequences synchronous to the played music file and/or audio file.

In summary: The control system architecture, in particular the software system architecture, may consist of three parts. The first part is a code running on the chip of the operating device of the portable light apparatus, responsible for generating light sequences and communicating via radio waves, in particular using low energy standard protocols and/or via BLE connection with a smartphone or a computer. The smartphone or computer application, as the central device, is the second part responsible for user account verification and data transmission to the glasses and acting as the main user interface/input device for the portable light apparatus. The third part of the system is a server back-end storing user data like payment info to verify and activate the use of the portable light apparatus as well as user account settings and data related to the use of the portable light apparatus. Because the desired stroboscopic light effect is best combined with auditory stimulation of the user, the light sequences will be automatically generated "on the fly" based on audio data input via low energy audio data and user preferred settings that may be controlled using the smartphone or computer application. Thus, no information is required for the light sequences to be encoded into a music file and/or an audio file, for example on different radio waves. In some designs, a brightness of the LEDs may be able to be manipulated through the normal user inputs used to regulate volume of a loudspeaker or headphones. Using the low energy audio standard, for example the BLE connection, the same audio data may be transmitted wirelessly to an actual loudspeaker or pair of headphones and the glasses at the same time. To be able to receive any incoming audio data, sent from the central device's operating system (OS) to the portable light apparatus, the portable light apparatus has to advertise themselves to the central device as speakers or headphones. The user settings for automated light sequence generation may be the number and order of effects with a frequency band for each effect and transitions between the effects or music titles and/or audio titles. The effects and transitions may be chosen from an effect library and manipulated to fit the user's wishes and needs—for example the stroboscopic frequency of the effect.

Therefore, the light sequencing algorithm may generate stroboscopic light sequences and/or frequencies on the fly based on audio data packages.

In some designs, a storage device may be provided to store user input data and/or music files and/or audio files.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The accompanying drawings which are given by way of illustration only, and thus, are not limiting the present invention, and wherein.

Corresponding parts are marked with the same reference symbols in all figures.

DETAILED DESCRIPTION OF SPECIFIC EMBODIMENTS

Figure 1:
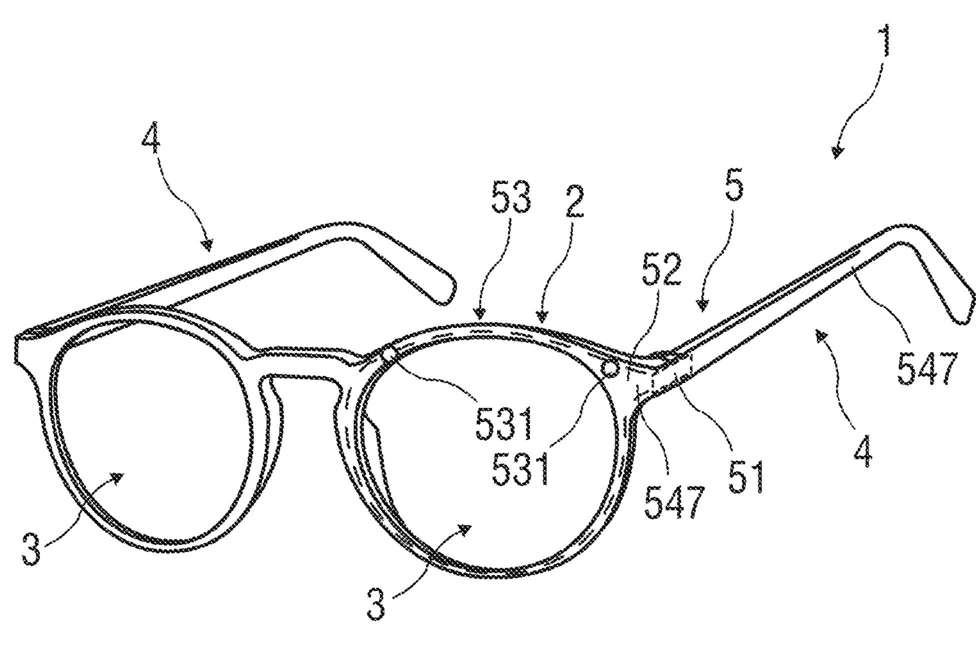
FIG. 1 schematically illustrates a perspective view of an embodiment of a portable light apparatus, comprising a front frame, a pair of side frames and an operating device having at least a battery and at least one auxiliary electronic part having a light device, wherein the battery is arranged in one of the side frames and the auxiliary electronic part and the light device is arranged in the front frame, FIG. 2 schematically illustrates a perspective view of an embodiment of a portable light apparatus, comprising a front frame, a pair of side frames and an operating device having a battery, a main electronic part and an auxiliary electronic part with a light device, wherein the battery and the main electronic part are arranged in one of the side frames and the auxiliary electronic part and the light device are arranged in the front frame, FIG. 3 schematically illustrates a detailed perspective view of the portable light apparatus according to FIG. 2, FIG. 4 schematically illustrates a perspective side view of the portable light apparatus according to FIG. 2, FIG. 5 schematically illustrates a perspective view of an embodiment of a charging case for a portable light apparatus, the charging case comprising at least a housing and a cavity in which the portable light apparatus is insertable to be held, protected and charged, FIG. 6 schematically illustrates a top view of the charging case according to FIG. 5 with an inserted portable light device, FIG. 7 schematically illustrates an embodiment of a control system providing remote control for a portable light apparatus to be worn by a user, the control system comprising at least a light sequencing algorithm and a communication interface, and FIG. 8 schematically illustrates an embodiment of a control and operating architecture for a portable light apparatus.

FIG. 1 shows schematically a perspective view of an embodiment of a portable light apparatus 1, in particular glasses, configured to be worn by a user.

The portable light apparatus 1 comprises a front frame 2 to house eyeglasses 3 and a pair of side frames 4 connected to the front frame 2. The portable light apparatus 1 further comprises an operating device 5 having a battery 51 and an auxiliary electronic part 52 having a light device 53 configured to emit light towards the eyeglasses 3 and/or the user's eyes. The light device 53 may comprise a number of light emitting diodes 531. The light emitting diodes 531, also called LEDs 531 may be arranged distributed on, in and/or over the front frame 2. In some designs, the LEDs 531 may be arranged partially or completely surrounding and/or encasing the front frame recesses for the eyeglasses 3. In some designs, the light device 53 is arranged in rims forming the front frame 2 for holding the eyeglasses 3.

The battery 51 is configured to supply energy to the light device 53 via the auxiliary electronic part 52. The battery 51, in particular a rechargeable battery 51, is arranged in one of the side frames 4 and the auxiliary electronic part 52 and the light device 53 are arranged in the front frame 2.

The auxiliary electronic part 52 may fully have the shape of the front frame 2. The auxiliary electronic part 52 may comprise LEDs 531 equally distributed around both eyeglasses 4 of the portable light apparatus 1.

Alternatively, the auxiliary electronic part 52 may have a shape of half of the front frame 2, for example in an eyeglass holding region. In some designs, two auxiliary electronic parts 52 may be arranged in the front frame 2. Each auxiliary electronic part 52 may have the shape of one eyeglass holding region. Each of the auxiliary electronic part 52 may comprise a respective light device 53.

Moreover, optionally additionally the portable light apparatus 1 may comprise at least one audio output device 547. The audio output device 547 is configured to output audio to the user.

The audio output device 547 may be arranged in at least one of the side frames 4. The audio output device 547 may be arranged in an area of the side frame 4 which is close to a user's ear when worn by the user. The audio output device 547 may comprise at least one loudspeaker and/or earphone and/or a bone sound transducer.

The audio output device 547 may at least be partially arranged in the front frame 2. In some designs, at least one loudspeaker, earphone and/or bone sound transducer may be arranged in the front frame 2. The audio output device 547 may be connected to the main electronic part 54. The audio output device 547 may comprise at least one interface to communicate with an external control device.

Figure 2:
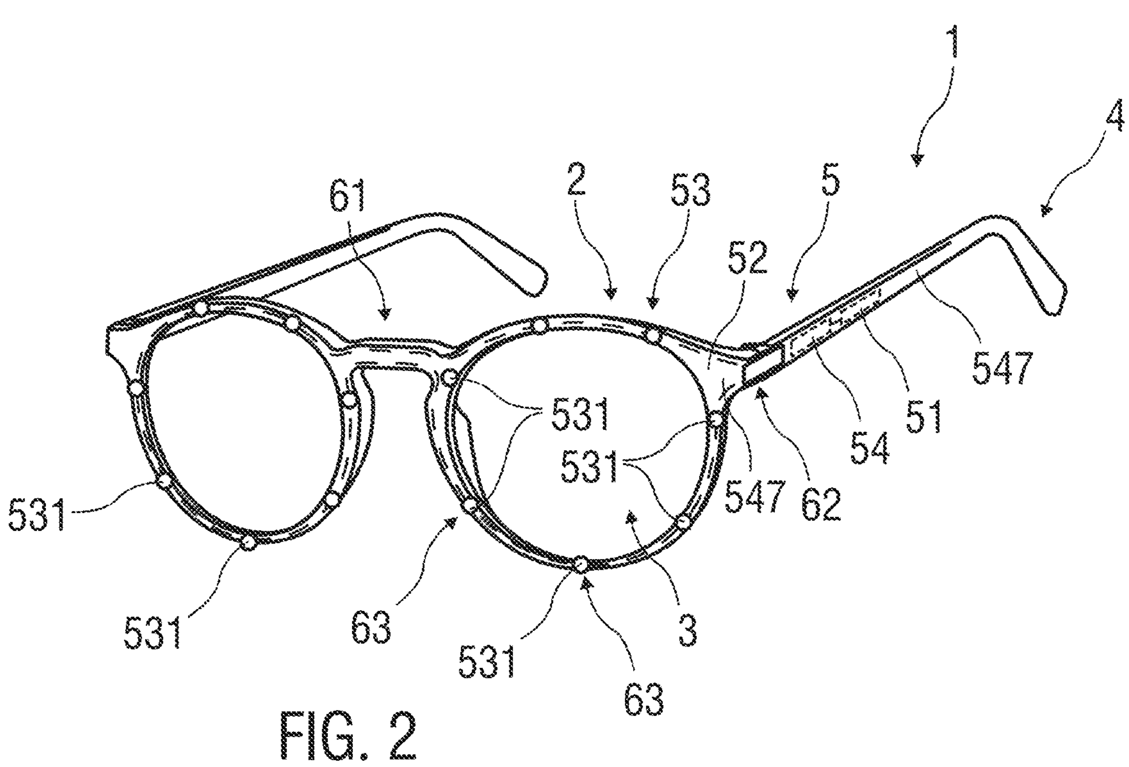

FIG. 2 shows schematically a perspective view of an embodiment of a portable light apparatus 1, comprising a front frame 2, a pair of side frames 4 and an operating device 5 having a battery 51, a main electronic part 54 and an auxiliary electronic part 52 with a light device 53, wherein the battery 51 and the main electronic part 54 are arranged in one of the side frames 4 and the auxiliary electronic part 52 and the light device 53 are arranged in the front frame 2.

In some designs, the auxiliary electronic part 52 is a flexible printed circuit board (flexible PCB, FPCB) which has an outline shape of the front frame 2. In some designs, the main electronic part 54 is a rigid printed circuit board (main PCB) with a number of electronic components.

In some designs, the auxiliary electronic part 52 comprises one bent area 61 in a nose bridge area. In some designs, the auxiliary electronic part 52 comprises a bent area 62 in a connection area 521 to at least one of the side frames 4, in particular to the main PCB. In some designs, the auxiliary electronic part 52 comprises a bent area 63 in an area of at least one light emitting diode 531 of the light device 53 to direct emitted light by the light device 53 towards the user's eye.

Moreover, optionally additionally the portable light apparatus 1 may comprise at least one audio output device 547. The audio output device 547 is configured to output audio to the user.

The audio output device 547 may be arranged in at least one of the side frames 4. The audio output device 547 may be arranged in an area of the side frame 4 which is close to a user's ear when worn by the user. The audio output device 547 may comprise at least one loudspeaker and/or earphone and/or a bone sound transducer.

The audio output device 547 may at least be partially arranged in the front frame 2. In some designs, at least one loudspeaker, earphone and/or bone sound transducer may be arranged in the front frame 2. The audio output device 547 may be connected to the main electronic part 54. The audio output device 547 may comprise at least one interface to communicate with an external control device.

Figure 3:
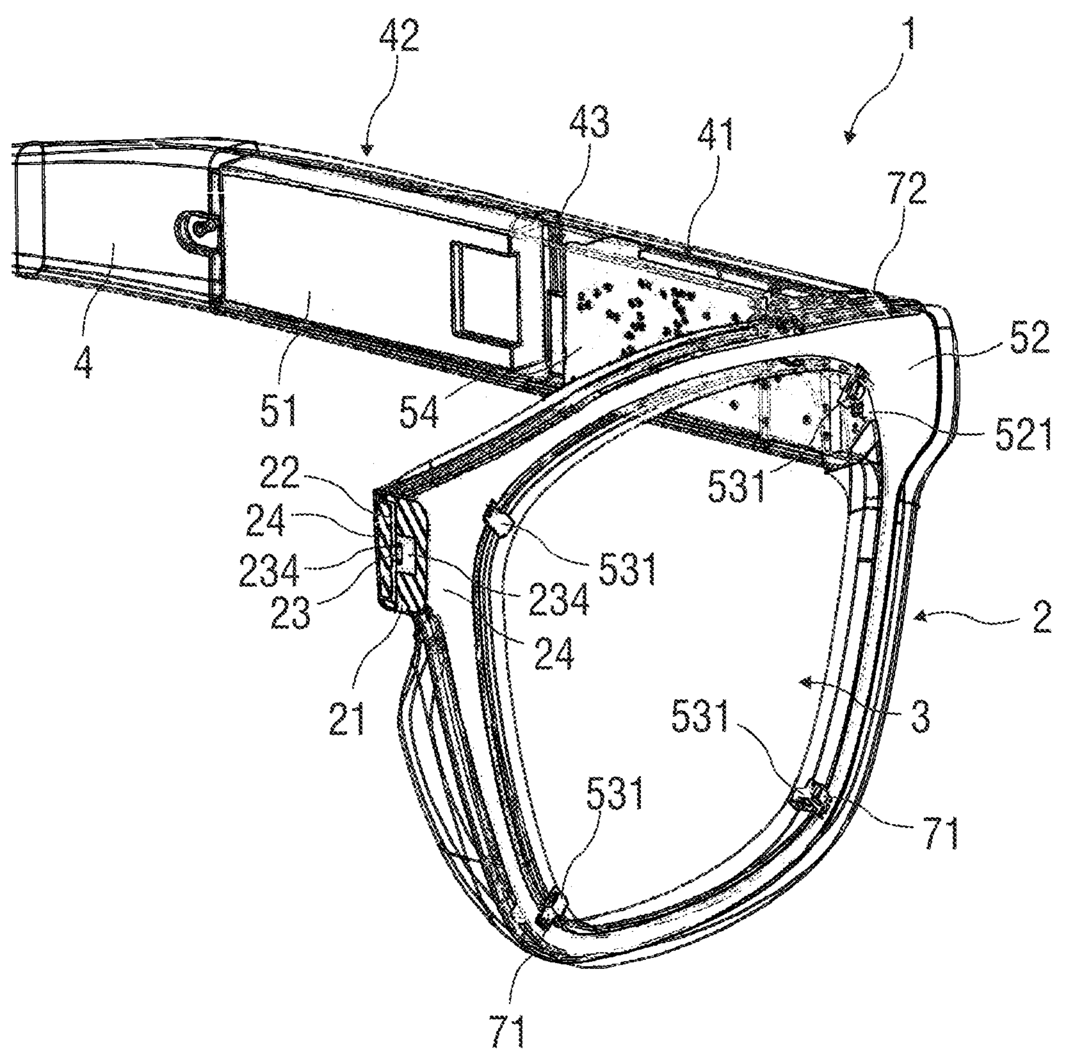

FIG. 3 shows schematically a detailed perspective view of the portable light apparatus 1 according to FIG. 2.

In some designs, the flexible auxiliary electronic part 52 has one stiffener layer 71 located in an area underneath the light device 53, in particular underneath each light emitting diode 531 of the light device 53. Each light emitting diode 531 is soldered to the flexible auxiliary electronic part 52.

In some designs, the flexible auxiliary electronic part 52 has one stiffener layer 72 located in an area underneath, above or both at the bent area 62 of the connection area 521 to at least one of the side frames 4 and/or to the main PCB to support the bend and connection.

The flexible auxiliary electronic part 52 is configured advantageously thin, so it may fit into any front frames 2 of glasses, in particular regular glasses, without changing its design and appearance as regular everyday glasses. The stiffener layers 71, 72 may support the flexible PCB in connection regions with other components of the portable light apparatus 1. The stiffener layers 71, 72 may be joined to the flexible PCB, for example by soldering or glue. The stiffener layers 71, 72 may be coatings or separate support plates.

The front frame 2 comprises two frame parts 21, 22, for example a front frame part 21 and a rear frame part 22, which are permanently or temporarily connected to one another to hold the eyeglasses 3.

In some designs, a fastening device 23 consisting of two corresponding fastening elements 234 is arranged in a nose bridge 24 of the front frame 2. The fastening device 23 may be one of a form-fitting device, a force-fitting device and/or material-fitting device for either a temporary or permanent connection of the frame parts 21, 22. The fastening elements 234 may be clip elements, clamping elements, snap-fit elements, adhesive elements, welding elements, screws, rivets or the like. In the shown embodiment the fastening elements 234 are configured as attracting magnet elements. The fastening device 23 is configured as a safe and reliable connection, in particular magnetic connection for simply detachable and connectable parts.

The frame parts 21, 22 are configured to hold and house the eyeglasses 3 and the auxiliary electronic part 52 with its light device 53. The front frame 2 is configured to house and embed the eyeglasses 3 and the auxiliary electronic part 52.

In one configuration, the front frame part 21, for example in in the area of the nose bridge 24, may be in cross-section substantially U-shaped or the like. The fastening elements 234 may be arranged in a respective recess formed in the nose bridge 24 of the front frame part 21 facing towards the rear frame part 22. The rear frame part 22 may have a respective size and shape corresponding with the form of the front frame part 21 in the area of the nose bridge 24. The nose bridge 24 of the rear frame part 22 is, for example, shaped as a bridge or web.

The front frame parts 21, 22 may comprise corresponding positioning elements, such as positioning pins and holes, clips, screws, rivets or other fastening and/or positioning elements. Alternatively or optionally additionally, the front frame parts 21, 22 may be coupled to each other by adhesive bonding, welding such as ultrasonic welding, soldering, overmolding and/or by a filling material such as potting compound.

The front frame 2 comprises two windows to encase the eyeglasses 3. The flexible auxiliary electronic part 52 may also comprise windows or cutouts corresponding with the size and shape of the windows of the front frame 2 so as to not block a vision of the user. The LEDs 531 of the light device 53 are also arranged in the front frame 2, in particular around the respective window, such that they do not block vision of the user when looking through the eyeglasses 3.

In the respective side frame 4 in which the battery 51 and the main electronic part 54 are arranged and safely housed, the main electronic part 54 is arranged in a front region 41 of the side frame 4 which is closer to the connection area 521 to the front frame 2. The battery 51 is located in a rear region 42 adjacent or behind the main electronic part 54. The main electronic part 54 connects the battery 51 with the flexible auxiliary electronic part 52 for energy control and energy supply. The connection between battery 51 and the main electronic part 54, that means to the main PCB, may be achieved by one of a common connection technique, for example via a cable device.

The respective side frame 4 may comprise a recess 43 to hold and encase the battery 51 and the main electronic part 54. The respective side frame 4 may also consist of two side frame parts which are permanently or temporarily coupled to each other. In some designs, the side frame parts may be joined together with magnets, snap fittings, glue, friction welding, overmolding or any other temporarily or permanent joining technique. Alternatively, the side frame 4 is configured as one-piece web or bridge housing respective components of the operating device 5.

Figure 4:
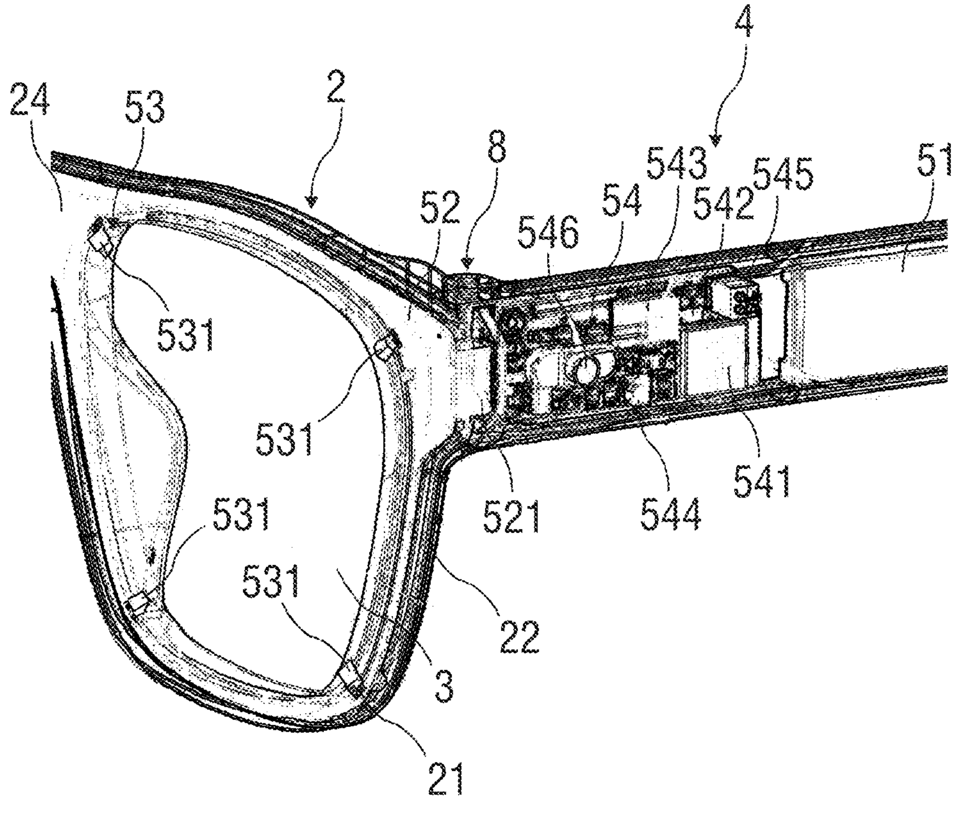

FIG. 4 shows schematically a perspective side view of the portable light apparatus 1 according to FIG. 2.

The front frame 2 is mechanically connected to the side frames 4, for example via a hinge joint 8 or any other connection mechanism. In some designs, the connection mechanism may be configured as a hinge and slide mechanism, for example a rotary-sliding hinge. In some designs, a pivot joint is configured as a sliding joint at the same time, wherein pivot movement of the side frame 4 relative to the front frame 2, when folding from the use state to the non-use state of glasses, causes the side frame 4 to slide relative to the front frame 2 or vice versa. The side frames 4 are foldable in a direction towards and away from the front frame 2. In some designs, one of the frame parts 21, 22 is connected to the side frames 4 via a respective hinge joint 8.

The portable light apparatus 1 may comprise a different wearing element than the side frames 4 connected to the front frame 2 to be worn by a user. The wearing element may be made from textile material. The wearing element may be a rubber band, headband or sweatband or the like to be worn by a user. The wearing element may embed, for example between different textile layers, at least the main electronic part 54 and the battery 51.

In an area of the respective hinge joint 8 between front frame 2 and the side frame 4, the flexible auxiliary electronic part 52 is connected to the main electronic part 54.

In some designs, the flexible auxiliary electronic part 52 is bent to create the connection area 521 between the flexible auxiliary electronic part 52 and the main electronic part 54. The connection area 521, in particular a connection and power interface, is arranged substantially perpendicular to a surface of a rear side facing towards the side frames 4 of the flexible auxiliary electronic part 52.

The operating device 5 comprises a processor module 541 on a chip held on the main PCB. The processor module 541 may comprise one or more processing cores. The operating device 5 comprises a radio module 542 coupled to the one or more processing cores to transmit and exchange data using radio waves. In some designs, the radio module 542 is configured to transmit and exchange data using low energy, for example using a Bluetooth Low Energy (BLE) connection. This is, for example, known from audio streaming over radio waves. In some designs, BLE Audio is configured to stream audio data.

Further, the operating device 5 comprises a light device driver 543 held on the main PCB to control stroboscopic frequency and/or light sequences of the light device 53. The main PCB may hold a multi-channel driver chip as the light device driver 543 to receive logic level signals from the processor module 541 to control stroboscopic frequency, for example for generating a light sequence, of the light device 53.

Further, the operating device 5 comprises a voltage regulation and battery charging circuitry 544 held on the main PCB to power the processor module 541 and the light device 53 on the flexible PCB and to recharge the battery 51.

In some designs, the operating device 5 comprises a charging connector 545, also called charging port or charging interface, which is arranged on the respective side frame 4. In one configuration, the charging connector 545 is arranged substantially perpendicular to a surface of the side frame 4. In another configuration, mating surfaces between the side frame 4 and the front frame 2 may house different charging interface elements. This arrangement allows a simple connection with a recharging device in a folded state of the portable light apparatus 1. The folded state refers to a commonly known fold technique of glasses.

In a further example, the operating device 5 comprises power switch 546 to connect a circuit of the main PCB to the battery 51 and to connect or disconnect all electrical components of the operating device 5 except the charging circuitry from the battery 51.

Figure 5:
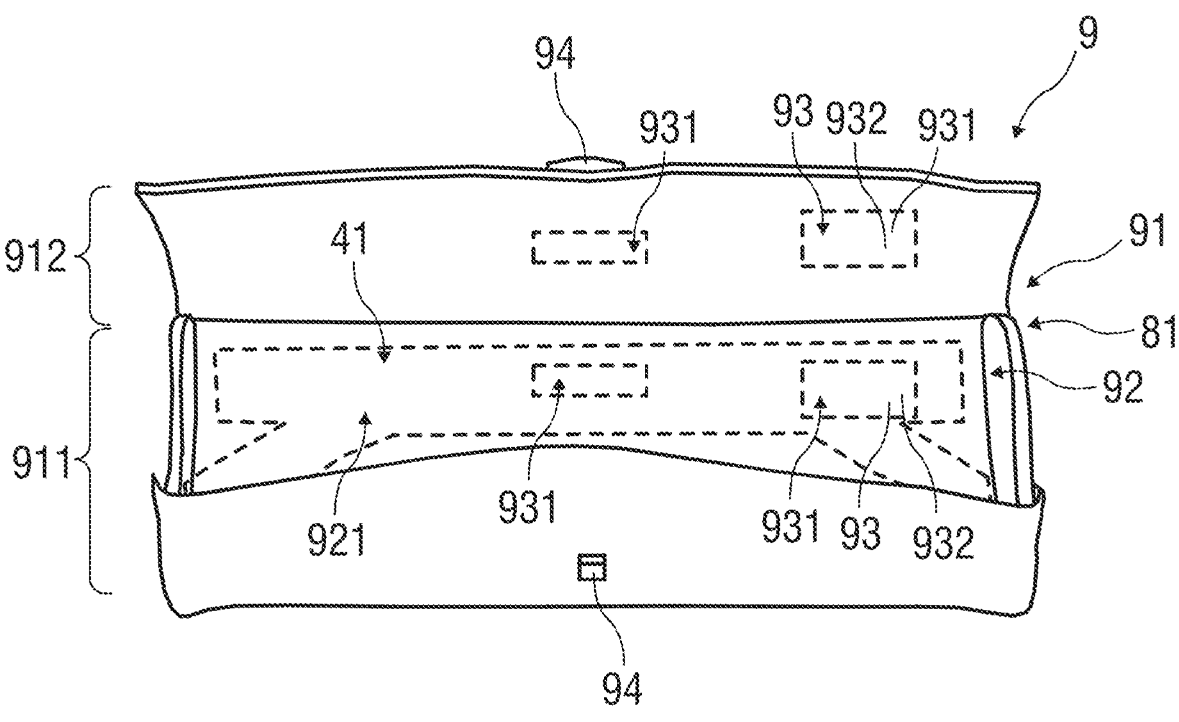

FIG. 5 shows schematically a perspective view of an embodiment of a charging case 9 for a portable light apparatus 1, the charging case 9 comprising a housing 91 and a cavity 92 in which the portable light apparatus 1 is insertable to be held, protected and charged.

The charging case 9 further comprises a charging operating device 93 arranged in the housing 91, wherein the charging operating device 93 is configured to charge the battery 51 of the portable light apparatus 1 when inserted in the cavity 92.

In some designs, the housing 91 comprises two corresponding housing parts 911, 912, for example a base housing part 911 and a secondary housing part 912 such as a flap or lid. The housing 91 and/or the housing parts 911, 912 may be made from hard shell and/or soft shell. One of the housing parts 911, 912, for example the base housing part 911, forms the cavity 92 and the other one of the housing parts 911, 912, for example the secondary housing part 912, is configured to close or open the cavity 92. The housing parts 911, 912 may be connected to each other by a hinge joint 81 to form the cavity 92 that may be opened and closed.

The housing parts 911, 912 contain magnets 94 that are oriented to attract the respective housing parts 911, 912. The housing parts 911, 912 may alternatively or optional additionally comprise other fasteners, such as clips and/or garment fasteners or the like.

In some designs, the cavity 92 is formed such that an insert direction, according to arrow A1, of the portable light apparatus 1 is defined for the user. The cavity 92 may be shaped such that the portable light apparatus 1 is tightly inserted and fitted in the cavity 92. The specified insert direction may refer to a specified folding configuration of the side frames 4. In some designs, the base housing part 911, in particular the cavity 92, may comprise a shaped recess 921 defining side frames 4 in a folded state.

In some designs, at least one of the housing parts 911, 912 comprises a holding element 913 configured to guide the user to insert and place the portable light apparatus 1 and to removably hold the portable light apparatus 1 in place in the cavity 92. In some designs, the holding element 913 is a magnet element which is arranged in an area of one of the housing parts 911, 912 corresponding with the location of a counter holding element located on the front frame 2 and/or the side frames 4 of the portable light apparatus 1. In some designs, the counter holding element may be provided by the integrated fastening device 23, for example the fastening elements 231, of the front frame 2.

The charging operating device 93 comprises a charging port 931 or connector which may be arranged in at least one of the housing parts 911, 912 to establish a temporary electrical connection to the portable light apparatus 1. The charging operating device 93 comprises charging electronics 932 which may be arranged in at least one of the housing parts 911, 912 for charging the battery 51 of the portable light apparatus 1. Charging electronics 932 may comprise at least one battery, such as a rechargeable battery.

Figure 6:
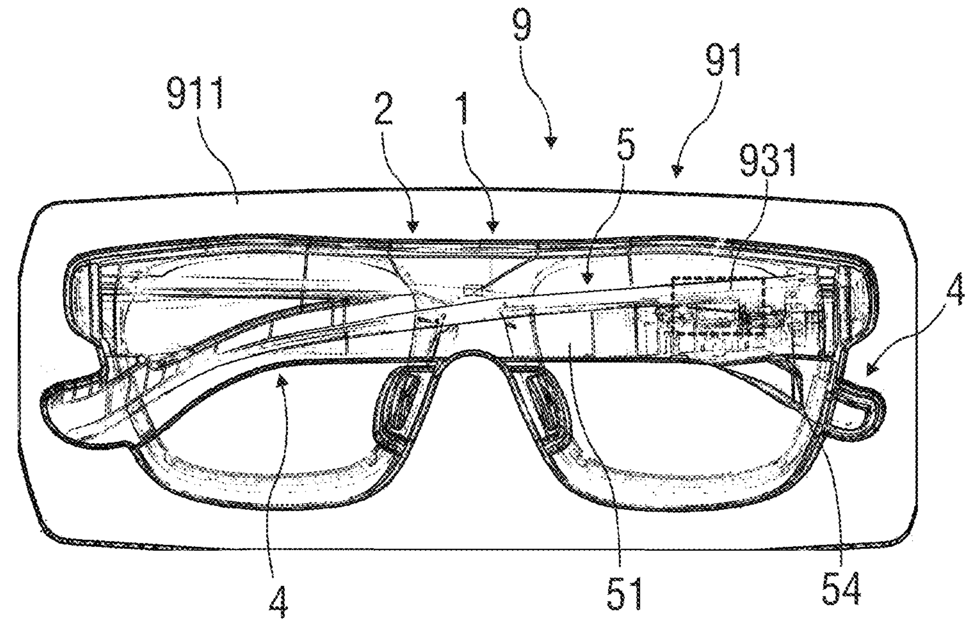

FIG. 6 shows schematically a top view of the charging case 9 according to FIG. 5 with an inserted portable light apparatus 1.

Shown is for example a bottom shell of the base housing part 911 on which the portable light apparatus 1 is placed when inserted in the cavity 92. An approximate location of the charging port 931 may be in an upper half on a right side or left side or lower half on a right side or left side of the housing part 911 depending on a predefined insert position of the portable light apparatus 1.

Figure 7:
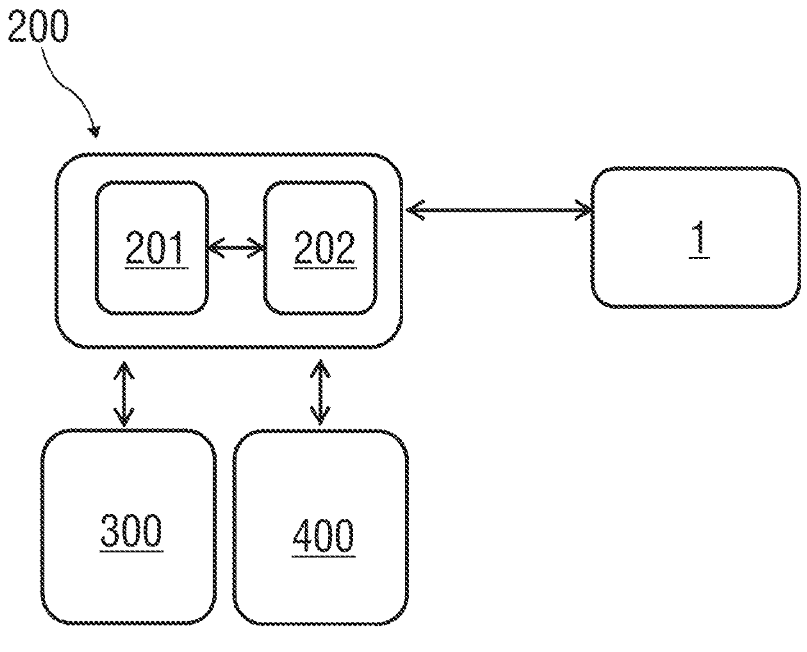

FIG. 7 shows schematically an embodiment of a control system 200 providing remote control for a portable light apparatus 1 to be worn by a user, the control system 200 comprising at least a light sequencing algorithm 201 and a communication interface 202.

The communication interface 202 provides connection to a mobile device 300 and/or a central server 400, wherein depending on data transmitted from the mobile device 300 and/or the central server 400 to the communication interface 202 the light sequencing algorithm 201 generates a light sequence for the portable light apparatus 1.

The control system 200 may be integrated in the portable light apparatus 1, for example held on the main electronic part 54 of the portable light apparatus 1.

The control system 200 may enable remote control for the portable light apparatus 1 so that the portable light apparatus 1 may be controlled from remote devices to allow a simple user interface. Furthermore, the control system 200 is configured to enable user engagement with the portable light apparatus 1 and social engagement between individual customers for example on a centralized platform for their own portable light apparatus 1.

The control system 200 may be configured as a processor module 541 or integrated in the processor module 541 of the portable light apparatus 1, for example of the operating device 5, to run the portable light apparatus 1. The control system 200 is an operating system and may be configured as software of the portable light apparatus 1.

The control system 200 is configured to be responsible to process at least one of the following described tasks. The control system 200 may be configured to receive audio data from an external source, such as the mobile device 300 and/or the central server 400, via radio waves. The control system 200 may be configured to manage software updates, wireless or wired. The control system 200 may be configured to retrieve, collect and exchange user data with the external source based on user settings. The control system 200 may be configured to store user input variables necessary to generate light sequences of the light device 53 of the portable light apparatus 1. The control system 200 may comprise a user authorization and activation based on input data from the mobile device 300, such as a smartphone or tablet, and/or the central server 400, for example from an application (short: APP), and/or from a server-side 500, for example a server-side device and/or back-end server and/or device, shown in FIG. 8.

The control system 200 may communicate with the mobile device 300 and/or the central server 400 to analyze, for example, played audio files and/or music files on the mobile device 300 and/or the central server 400 and to synchronize and/or generate an appropriate light frequency and/or light sequence of the light device 53 according to the audio file and/or music file listened by the user. The communication interface 202 is configured to exchange audio data based on low energy, for example via radio waves. The communication interface 202 may be configured to exchange audio data over Bluetooth Low Energy (BLE) connection.

In some designs, the light sequencing algorithm 201 is configured to generate light sequences based on received audio data and/or user settings.

In some designs, the light sequencing algorithm 201 is configured to analyze audio data packages that are received via radio waves on the fly, meaning as soon as they arrive. Information generated based on the analyzed audio data packages alongside the input of a number of user input variables from sequencing settings may then be used to generate light sequences to the played music file and/or audio file on the mobile device 300 and/or central server 400.

Figure 8:
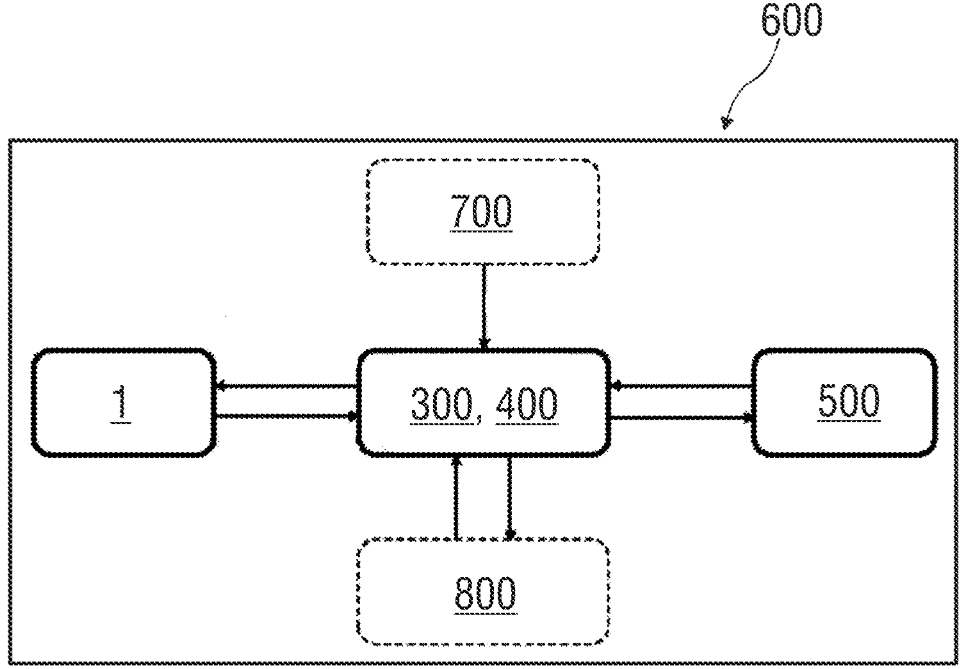

FIG. 8 shows schematically an embodiment of a control and operating architecture 600, also called "Strobes System" for a portable light apparatus 1.

The architecture 600 of a system to control and operate the portable light apparatus 1 comprises multiple main components. The system's hardware consists of the portable light apparatus 1 and the charging case 9. Software may consist of, for example, three subsystems. One subsystem may be embedded software in the portable light apparatus 1. The embedded software may comprise the control system 200 of the portable light apparatus 1. One subsystem may be the mobile device 300 and/or the central server 400. One subsystem may be services provided by the server-side 500.

The whole system may be used in the following way, for example from a perspective of a company: The hardware consisting of the portable light apparatus 1 and the charging case 9 may be shipped to a customer who has created a user account and paid their fees. As hardware the user may additionally use output devices 800, such as headphones or loudspeakers.

In some designs, an automated sequence generator may provide a service for the use of a stroboscopic light sequences. The interaction between the portable light apparatus 1 and the central server 400 may be based on a monthly or an annual subscription payment. The user payment and/or subscription information may be stored in the server-side 500 and will be needed for activation of the stroboscopic light features of the portable light apparatus 1 via the central server 400, which means via an APP.

If the user does not activate the portable light apparatus 1 or continue to pay the subscription after ending of a paid period, all features will be disabled until the payment is continued. Under these circumstances, the portable light apparatus 1 could only be used as regular glasses or sunglasses. The application may provide functionality to collect data anonymously like use duration and use mode, which may enable better understanding of needs of customers.

The application will also have a "voluntary survey for research"—feature to collect more detailed data turning users into probands, which will be the scientific foundation to prove efficacy of "use protocols" for different conditions in clinical trials. The protocols will later be provided in professional license training units for medical professionals, to show how to use the portable light apparatus 1, in particular as light therapy apparatus, for different patient conditions.

Every user will have the "Album" or "Playlist" feature that enables them to store and share the settings they are using with different audio tracks and/or music tracks. The audio tracks and/or music tracks may be stored on the user's mobile device 300 and/or the central server 400. When the mobile device 300 and/or the central server 400 is connected to the output device 800, the user may listen to the respective tracks in combination with the application of light sequences.

The playlists may be made publicly available, be kept in privacy or shared with everyone and/or only selected users. This way, users may share their experience with each other and licensed practitioners will have the ability to share their sequences with their patients.

The album function will also come with a "commentary" and "like" function, for all shared albums. This way all types of users will be able to give each other feedback on their experiences which will help to improve everyone's experiences and enhance the social engagement aspect.

Private album information may be stored locally on the smartphone or computer or be stored in the server-side database to be available and used from devices capable of using audio data, for example on low energy and/or via BLE.

Lastly, a use-case/feature is provided called "party mode" which will be available for all users. This mode may be used locally when multiple people using the so called "Strobes System", so all portable light apparatus 1 may be synchronized to receive data from a single source so they will generate the same stroboscopic effects for every user. To locally increase signal range and cover large festival areas, long range antennas for the portable light apparatus 1 to receive input data over long distances, for example up to at least 1 km, may be used and integrated. In some designs the so called "Strobes System" may be extended by using a local streaming terminal or router, that houses long range antennas to transmit signals over low energy radio waves. This way, it may not be necessary to include long range antennas into the portable light apparatus 1 decreasing weight, size and potentially saving battery charge therefore enhancing user experience. The same synchronous effect may also be achieved, through streaming data provided by the central server 400 and/or a streaming service 700 to the portable light apparatus 1. This in return may enable large virtual parties around the globe to experience custom sight sequences adapted to their music.

The use of the portable light apparatus 1 is not limited to the above mentioned so called "Strobes System".

The so called "Strobes System" may be extended by utilizing multiple sensors, for data collection and data input, as well as multiple output devices. The sensors may include but are not limited to: heartrate sensor, blood pressure sensor, blood oxygen sensor, EEG—electroencephalography measurement data and fMRI—functional magnetic resonance imaging. The output devices that may be utilized to extend the "Strobes System" may include, but are not limited to: transcutaneous electrical nerve stimulation devices, electric actuators that create mechanical oscillations which may be felt by the user via touch.

Those of skill in the art will understand that modifications (additions and/or removals) of various components of the apparatuses, methods and/or systems and embodiments described herein may be made without departing from the full scope and spirit of the present invention, which encompass such modifications and any and all equivalents thereof.

A list of embodiments follows:

Embodiment 1: A portable light apparatus is configured to be worn by a user, the portable light apparatus comprising at least:

- a front frame to house eyeglasses and a pair of side frames connected to the front frame,
- an operating device having at least a battery, at least one main electronic part and at least one auxiliary electronic part having a light device configured to emit light towards the eye-glasses and/or the user's eyes,
- wherein the battery is configured to supply energy to the light device via the electronic parts,
- wherein the main electronic part comprises a number of interfaces to couple with an external charging device to recharge the battery and/or to couple with an external control device.

Embodiment 2: Portable light apparatus according to embodiment 1, wherein the battery and the main electronic part are arranged in one of the side frames and the auxiliary electronic part with the light device is arranged in the front frame.

Embodiment 3: Portable light apparatus according to embodiment 1 or 2, wherein the auxiliary electronic part is a flexible printed circuit board which has an outline shape of the front frame.

Embodiment 4: Portable light apparatus according to embodiment 1 or 2, wherein the main electronic part is a printed circuit board having an interface providing a connection to the auxiliary electronic part and an interface providing a connection to the battery.

Embodiment 5: Portable light apparatus according to embodiment 1 or 2, wherein the auxiliary electronic part comprises at least one bent area in a nose bridge area, a connection area to at least one of the side frames and/or in an area of at least one light emitting diode of the light device.

Embodiment 6: Portable light apparatus according to embodiment 1 or 2, wherein the front frame comprises two frame parts permanently or temporarily connected to one another to hold the eyeglasses and the auxiliary electronic part with its light device.

Embodiment 7: Portable light apparatus according to embodiment 6, wherein in a detached state of the front frame the eyeglasses are exchangeable and wherein the auxiliary electronic part and the light device are held in one of the frame parts.

Embodiment 8: Portable light apparatus according to embodiment 1 or 2, wherein the operating device comprises a communication interface providing connection to a mobile device, a central server and/or a server-side device to exchange user data and/or to control the operating device from the mobile device, the central server and/or the server-side device.

Embodiment 9: Portable light apparatus according to embodiment 1 or 2, wherein the operating device comprises a light device driver to control stroboscopic frequency and/or light sequences of the light device in the front frame.

Embodiment 10: Portable light apparatus according to embodiment 1 or 2, wherein the eyeglasses are configured as regular transparent or colored glasses, ophthalmic grade glasses, color tinted glasses and/or functionally coated glasses and/or thermochromic coated glasses and/or electrochromic coated glasses.

Embodiment 11: Charging case for a portable light apparatus which is configured to be worn by a user, the charging device comprising at least:

a housing having a cavity in which the portable light apparatus is insertable to be held and protected, and a charging operating device arranged in the housing, wherein the charging operating device is configured to charge a battery of the portable light apparatus when inserted in the cavity.

Embodiment 12: Charging case according to embodiment 11, wherein the housing comprises two corresponding housing parts, wherein one of the housing parts forms the cavity and the other one of the housing parts is configured as a lid or flap to close or open the cavity.

Embodiment 13: Charging case according to embodiment 11 or 12, wherein the cavity is formed such that an insert direction of the portable light apparatus is defined for the user.

Embodiment 14: Charging case according to embodiment 12 or 13, wherein at least one of the housing parts comprises a holding element configured to guide the user to insert the light apparatus and to removably hold the portable light apparatus in place in the cavity.

Embodiment 15: Charging case according to embodiment 11 or 12, wherein the housing comprises charging electronics for charging the portable light apparatus and at least one charging port to establish a temporary electrical connection to the portable light apparatus.

Embodiment 16: Control system providing remote control for a portable light apparatus to be worn by a user, the control system comprising at least:

a light sequencing algorithm and a communication interface providing connection to a mobile device and/or a central server, wherein depending on data transmitted from the mobile device and/or the central server to the communication interface the light sequencing algorithm generates a light sequence for the portable light apparatus.

Embodiment 17: Control system according to embodiment 16, wherein the communication interface is configured to provide communication to a server-side device for user authorization of the portable light apparatus.

Embodiment 18: Control system according to embodiment 16 or 17, wherein the communication interface is configured to communicate audio data, in particular via radio waves.

Embodiment 19: Control system according to embodiment 16 or 17, wherein the light sequencing algorithm is configured to generate light sequences based on received audio data and/or synchronous to music files and/or audio files playing on the mobile device and/or the central server.

Embodiment 20: Control system according to embodiment 16 or 17, wherein the light sequencing algorithm is configured to generate light sequences based on received audio data and/or user settings.

LIST OF REFERENCES

1 portable light apparatus
2 front frame
21, 22 frame part
23 fastening device
231 fastening element
24 nose bridge
3 eyeglasses
4 side frame
41 front region
42 rear region
43 recess
5 operating device
51 battery
52 auxiliary electronic part
521 connection area
53 light device
531 light emitting diode
54 main electronic part
541 processor module
542 radio module
543 light device driver
54 voltage regulation and battery charging circuitry
545 charging connector
546 power switch
61 to 63 bent area
71, 72 stiffener layer
8, 81 hinge joint
9 charging case
91 housing
911, 912 housing part
913 holding element
92 cavity 921 recess
93 charging operating device
931 charging port
932 charging electronics
94 magnet
200 control system
201 light sequencing algorithm
202 communication interface
300 mobile device
400 central server
500 server-side
600 architecture
700 streaming service
800 output device
A1 arrow

What is claimed is:

1. A system comprising at least:

a portable light apparatus to be worn by a user having a front frame to house eyeglasses, an operating device having at least one electronic part and a light device, the light device being arranged in the front frame and configured to emit light towards the eyeglasses and/or the user's eyes, and a mobile device and/or a central server, wherein the operating device of said portable light apparatus comprises a control system comprising at least a light sequencing algorithm and a communication interface providing connection to the mobile device and/or the central server, wherein the communication interface is configured to receive audio data, wherein the light sequencing algorithm is configured to analyze audio data packages depending on data transmitted from the mobile device and/or the central server to the communication interface, wherein the light sequencing algorithm generates a light sequence for the portable light apparatus in real-time based on the audio data packages.

2. The system according to claim 1, wherein the communication interface is configured to provide communication to a server-side device for user authorization of the portable light apparatus.

3. A portable light apparatus configured to be worn by a user comprising a system according to claim 2, the portable light apparatus further comprising at least:

a pair of side frames connected to the front frame, the operating device having at least a battery configured to supply energy to the light device via the electronic part.

4. The portable light apparatus according to claim 3, wherein the control system comprises a processor module integrated on the operating device.

5. The system according to claim 1, wherein the communication interface is configured to communicate audio data, in particular via radio waves.

6. A portable light apparatus configured to be worn by a user comprising a system according to claim 5, the portable light apparatus further comprising at least:

a pair of side frames connected to the front frame, the operating device having at least a battery configured to supply energy to the light device via the electronic part.

7. The system according to claim 1, wherein the light sequencing algorithm is configured to generate light sequences based on received audio data from the mobile device and/or the central server.

8. A portable light apparatus configured to be worn by a user comprising a system according to claim 7, the portable light apparatus further comprising at least:

a pair of side frames connected to the front frame, the operating device having at least a battery configured to supply energy to the light device via the electronic part.

9. The system according to claim 1, wherein the light sequencing algorithm is configured to generate light sequences based on audio files playing on the mobile device and/or the central server.

10. A portable light apparatus configured to be worn by a user comprising a system according to claim 9, the portable light apparatus further comprising at least:

a pair of side frames connected to the front frame, the operating device having at least a battery configured to supply energy to the light device via the electronic part.

11. The system according to claim 1, wherein the light sequencing algorithm is configured to generate light sequences based on user settings via the mobile device and/or the central server.

12. A portable light apparatus configured to be worn by a user comprising a system according to claim 11, the portable light apparatus further comprising at least:

a pair of side frames connected to the front frame, the operating device having at least a battery configured to supply energy to the light device via the electronic part.

13. The system according to claim 1, comprising at least a transmitting unit which is configured to transmit received audio data to an audio amplifier or audio output device.

14. The system according to claim 13, wherein the transmitting unit is configured to share or forward data with devices that use same radio wave communication interfaces.

15. A portable light apparatus configured to be worn by a user comprising a system according to claim 14, the portable light apparatus further comprising at least:

a pair of side frames connected to the front frame, the operating device having at least a battery configured to supply energy to the light device via the electronic part.

16. A portable light apparatus configured to be worn by a user comprising a system according to claim 13, the portable light apparatus further comprising at least:

a pair of side frames connected to the front frame, the operating device having at least a battery configured to supply energy to the light device via the electronic part.

17. The system according to claim 1, wherein the light sequencing algorithm is configured to analyze audio data packages that are received via radio waves, wherein information, generated based on the analyzed audio data packages alongside the input of a number of user input variables from sequencing settings via the mobile device and/or the central server, are used to generate light sequences synchronous to the played music file and/or audio file.

18. A portable light apparatus configured to be worn by a user comprising a system according to claim 17, the portable light apparatus further comprising at least:

a pair of side frames connected to the front frame, the operating device having at least a battery configured to supply energy to the light device via the electronic part.

19. A portable light apparatus configured to be worn by a user comprising a system according to claim 1, the portable light apparatus further comprising at least:

a pair of side frames connected to the front frame, the operating device having at least a battery configured to supply energy to the light device via the electronic part.

20. The portable light apparatus according to claim 19, wherein the control system comprises a processor module integrated on the operating device.

* * * * *